United States Patent [19]

Glodo et al.

[11] Patent Number: 4,524,420

[45] Date of Patent: Jun. 18, 1985

[54] SIGNAL PROCESSING APPARATUS

[75] Inventors: David O. Glodo; James McFaddin, both of Dallas, Tex.

[73] Assignee: Core Laboratories, Inc., Dallas, Tex.

[21] Appl. No.: 411,522

[22] Filed: Aug. 25, 1982

[51] Int. Cl.³ .............................................. G06F 15/20
[52] U.S. Cl. .................................................... 364/497
[58] Field of Search ...................... 364/497, 498, 722; 73/23.1

[56] References Cited

U.S. PATENT DOCUMENTS

| | | | |
|---|---|---|---|
| 3,488,480 | 1/1970 | Stacy | 364/497 |
| 3,555,260 | 1/1971 | Karohl | 364/497 |
| 3,614,408 | 10/1971 | Watkin et al. | 364/497 X |
| 3,732,411 | 5/1973 | Galeener | 364/497 |
| 3,746,982 | 7/1973 | Allington | 364/497 X |
| 3,797,300 | 3/1974 | Sato | 364/497 X |
| 4,089,060 | 5/1978 | Mitchell | 364/722 |
| 4,229,968 | 10/1980 | Muldoon | 364/497 X |
| 4,232,233 | 11/1980 | Clouser et al. | 328/145 X |
| 4,255,793 | 3/1981 | Nakamura | 364/722 X |
| 4,266,277 | 5/1981 | Issenmann | 364/498 |
| 4,338,589 | 7/1982 | Engel et al. | 364/722 X |
| 4,374,424 | 2/1983 | Coustre et al. | 364/497 |
| 4,397,958 | 8/1983 | Vroom | 364/497 X |

FOREIGN PATENT DOCUMENTS

| | | |
|---|---|---|
| 930972 | 7/1963 | United Kingdom . |
| 1102744 | 2/1968 | United Kingdom . |
| 1204509 | 9/1970 | United Kingdom . |
| 1253090 | 11/1971 | United Kingdom . |
| 1306351 | 2/1973 | United Kingdom . |
| 1309761 | 3/1973 | United Kingdom . |
| 1355026 | 5/1974 | United Kingdom . |

Primary Examiner—Edward J. Wise
Attorney, Agent, or Firm—Lee C. Robinson, Jr.

[57] ABSTRACT

Apparatus for processing the output signal of a gas chromatograph. An interface device receives the analog output signal and digitizes it, reducing the effects of noise and preparing the signal for processing by a digital microprocessor. The microprocessor detects and measures peaks in the signal and determines the desired identification (in order of ascending molecular weight) and concentration (peak amplitude) data. A logarithmic output signal is produced for displaying output signals with wide dynamic ranges on a strip chart recorder.

24 Claims, 2 Drawing Figures

SIGNAL PROCESSING APPARATUS

BACKGROUND OF THE INVENTION

This invention relates to signal processing apparatus, and more particularly to interfacing apparatus for analyzing and displaying the output signals from a gas chromatograph.

The present invention is applicable generally to the processing and display of electrical signals, for example where it is desirable to analyze and display the waveform of a signal with a wide dynamic range and minimize the effect of any noise on the signal. It is particularly well suited to the analysis of the hydrocarbon content of drilling mud as it is circulated into and out of an oil or gas well during rotary drilling operations. During the rotary drilling of a well, the drilling mud, which is a suspension of oil, water, and various solids, is pumped down the hollow drill string to the bottom of the well, exits through holes in the drill bit, and returns to the surface through the annular space between the drill string and the borehole wall. Among the functions of drilling mud are cooling the drill bit, carrying rock cuttings to the surface, and sealing the borehole wall. It has also been recognized that the drilling mud returning to the top of the well often contains detectable quantities of any hydrocarbons that are present in the pore spaces of the underground formations penetrated by the borehole. Analysis of the mud is therefore useful to determine the hydrocarbon content of subterranean strata currently under exploration.

The detection and differentiation of the various hydrocarbon components present in drilling mud is most rapidly and economically accomplished by gas chromatography. A sample of a gaseous mixture to be analyzed is introduced into a column containing a medium which retards the passage of the individual components of the sample to differing degrees that are roughly correlated to the logarithms of the respective molecular weights of the components. A carrier gas is directed through the column to elute the constituents from the medium in sequence. At the output end, the quantity of each component is then measured by a gas detector, for example of the flame ionization type, such as that used in the Varian 940 gas chromatograph. Alternative types such as the hot-wire detector, which measures the thermal conductivity of the effluent gas from the column, may also be used. The column is calibrated by passing known, pure gases through it and measuring the peak amplitudes of the respective hydrocarbon components.

The operating cycle of a chromatograph generally comprises at least a forward phase, in which the flow of carrier gas is maintained in the forward direction long enough for all detectable components of the gas mixture to be eluted. There is also a reverse phase in which the column is backflushed in order to ready the column for the next sample. As an alternative, if it is desired to measure only lighter components, the flow can be reversed after the desired hydrocarbons have been eluted and measured, and only the heavier residual components are backflushed into the atmosphere. In yet another system, the heavier ends are conducted after backflushing not to the atmosphere, but rather to the gas detector for analysis in bulk.

The thermal conductivity cell of a hot-wire detector or the electrometer of a flame ionization detector produces as the output of the chromatograph an analog signal whose voltage is representative of the quantity of materials detected at a particular point in time. This signal is generally displayed on a chart recorder in the form of a chromatogram, which is a graph including one or a plurality of curves, each peak to the curves corresponding to one detected component of the specimen. The composition of the specimen can then be determined by comparing the chromatogram of the specimen with previously produced chromatograms of a known substance, because the location of each peak on the chromatogram indicates the elution time between the commencement of measurement and the arrival of the component substance at the output end of the chromatograph tube, and thus indicates the unique molecular weight of the component substance. Quantity and concentration data can be determined from the amplitude of the chromatogram curve over time.

In order to measure component quantities which may vary by many orders of magnitude, attenuating or amplifying devices are typically associated either with the chromatograph, the chart recorder, or an interface or signal processing device linking the two. This feature brings the output signal to a level within the full-scale range of the recorder and is necessary in order to keep the pen on the chart and to have a readable curve for both very large and very small concentrations of a component. These scaling devices may be either manual or automatic, and include either manual switches or analog or digital devices that perform the functions of sensing the range of the magnitude of the output signal and attenuating or boosting the signal accordingly.

Analog or digital systems are also used to electronically integrate the signal over time for each peak, thus determining the area below the chromatogram curve, and above a baseline level, the latter level representing the output signal owing solely to the detected carrier gas, plus noise. This area is a measure of the quantity of component substance detected, and thus can be used to determine the concentration of each component substance in the total specimen. Autozero devices may be used to set the baseline curve at the zero point on the output graph.

This invention is intended to address certain recurring problems with prior chromatograph interfaces. First is the problem of noise. As stated previously, the desired analysis of a test specimen can be derived from the sequential series of peaks of a chromatogram on the basis of, first, the peak emergence time to identify the components of the sample, and second, the amplitude of the peak to indicate their concentrations. Peaks may be well resolved, or, on the other hand, a chromatograph may be complex, containing many peaks, some only partially resolved. The digital or analog device that processes the signal must sense the occurrence of a peak, measure the peak amplitude, provide for separating overlapping peaks, and allow for the baseline signal.

Each of these functions can be impaired by noise. One type is the ordinary 60 Hertz line noise from power supplies, amplifiers, and readouts. Electrical noise can also arise from voltage surges from sources unrelated to the chromatograph, or internal spikes, for example from particulate matter entering a detector. High-frequency detector noise may also be produced, for example, by impurities or flow irregularities in the fuel gas of a flame ionization detector, or by sensitivity to carrier gas flow or filament movement in a hot-wire detector.

Pneumatic noise may arise from an unwanted baseline change due to loss of retarding medium, or changes in the flow of the carrier gas either inherent in the pumping or regulating devices or due to leaks or faulty components. Chemical or physical noise can be due to contamination of the chromatograph column or displacement of the materials therein.

Prior systems have required that complex smoothing, weighting, or slope-averaging functions be performed in order to determine whether spikes or flat signal portions are noise or signal. It is desired that an apparatus be provided to compensate for noise in a simpler way.

Another problem to be addressed is flexibility of display and analysis of the chromatograph signal. In conventional display systems the output to the chart recorder commonly is switched either automatically or manually to a range appropriate to the magnitude of the signal. It would be desirable for the number of such ranges to be minimized, for the dynamic range of signals that can be accommodated without such switching to be increased, and for the operator to be informed when the measurement range of the instrumentation has been exceeded.

Further, it is desirable that the signal analysis device be easily adaptable to changes in the mode of analysis, have automatic features enabling it to operate automatically to the greatest extent possible, and be accurate and reliable.

OBJECTS AND SUMMARY OF THE INVENTION

One general object of this invention, therefore, is to provide new and improved interfacing apparatus for analyzing and displaying output signals from a gas chromatograph.

More specifically, it is an object of the invention to minimize the adverse effect of noise, and in particular electrical noise, on the analysis of data signals from a gas chromatograph.

Another object of the invention is to provide means for displaying signals of increased dynamic range on a chart recorder and to minimize the range switching that must be done in order to accommodate signals of varying dynamic range.

A further object of the invention is to provide reliable, accurate, automatic, and flexible analysis of the output signal from a gas chromatograph.

Yet another object of the invention is to detect peak amplitudes of the chromatograph signal and to sound an alarm device when the measurement range of the instrumentation has been exceeded.

One general feature of the disclosed embodiments of the invention provides for logarithmic conversion of the chromatograph signal before it is displayed. This compresses the range of the signal, allowing the display on a chart recorder of output signals having a wide dynamic range, while minimizing or eliminating the need for scale switching. A dynamic range of five decades can be accommodated without range switching.

In one embodiment, the chromatograph signal is digitized and transmitted to a digital microprocessor. The microprocessor samples the amplitude of the input signal repeatedly and produces an output signal equal to its logarithm, which is displayed as previously described.

Also, in this embodiment the digitization process is performed by a voltage-to-frequency converter, the output pulses of which are accumulated and counted at least ten times per second. This frequency of sampling results in an averaging of the random effects of electrical noise, and the effect of such noise on peak detection, integration, and baseline calculation is therefore minimized.

Further, automatic features are provided for sensing the output range of the gas chromatograph with which the interface apparatus is used, and activating an alarm device when the dynamic range of the apparatus is exceeded. As a further automatic feature, the interface senses the forward analysis phase of the chromatograph and begins its signal processing functions in response. Finally, the use of a microprocessor allows for changes at will in the method of analysis or output format, as well as increased accuracy over analog systems which are based on the charging of a capacitor.

In another disclosed embodiment, the logarithmic conversion of the chromatograph signal is by a logarithmic analog amplifier, which is useful in applications or environments where it is possible that the functioning of the microprocessor may be interrupted.

By these features, the aforesaid objects of improved noise reduction, efficiency or display, and reliable, accurate, automatic, and flexible operation are achieved. The invention, as well as further objects and advantages thereof, will be understood more clearly and fully from the following description of the disclosed embodiments, when read with reference to the accompanying drawings, in which like reference numerals denote like elements and parts.

DESCRIPTION OF THE DISCLOSED EMBODIMENTS

Figure 1:
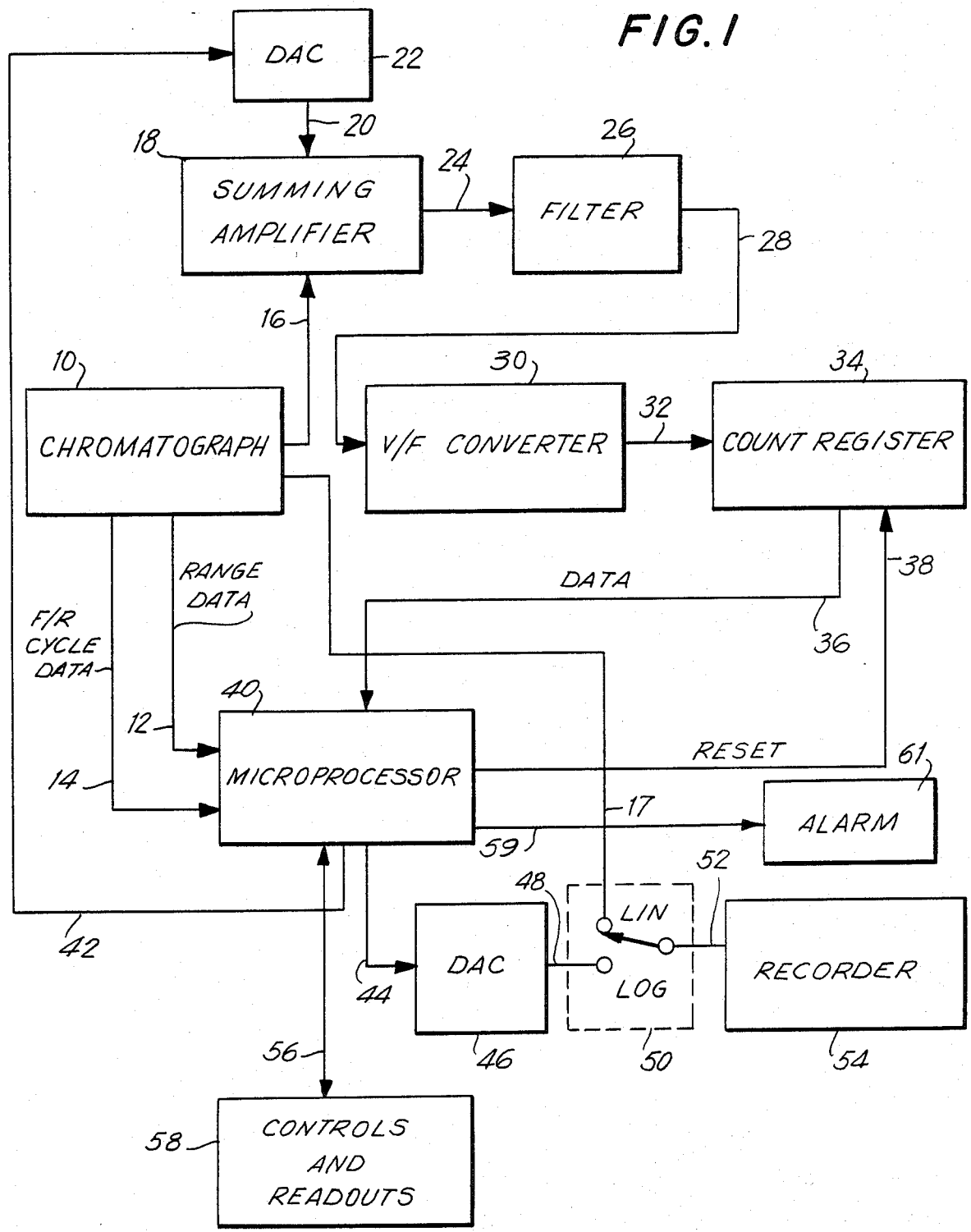
FIGS. 1 and 2 are block diagrams showing interface apparatus according to two illustrative embodiments of the invention.

Referring to FIG. 1 of the drawings, the analysis of a sample substance is performed by a chromatograph 10. One appropriate unit for use in the analysis of drilling mud from an oil or gas well is available commercially from Varian Associates, Inc., Palo Alto, Calif., and is identified as the Varian 940 Gas Chromatograph, although others can also be used. The chromatograph advantageously is capable of detecting hydrocarbon compounds containing from one to six carbon molecules in quantities varying over a dynamic range of at least five decades. The sensitivity to compounds with one molecule preferably is at least from $10^1$ ppm to $10^6$ ppm. The chromatograph is capable of use both in the laboratory and in the field.

The interface apparatus of the present embodiment is useful, inter alia, with a chromatograph of the flame ionization type having an electrometer detector. The sensitivity range in such devices can be detected on an output lead 12. Another output lead 14 provides a signal indicating whether the chromatograph is in its forward or reverse phase. Output leads 16 and 17 carry the output signal of the electrometer of the chromatograph, the lead 16 being one input to a summing amplifier 18.

The other input to the summing amplifier 18 is carried by a lead 20 from the output of a digital-to-analog converter 22. The output of the amplifier 18 is fed by a lead 24 to a filter 26, whose output by way of a lead 28 is the input to a voltage-to-frequency converter 30. The converter 30 produces pulses that are transmitted by a lead 32 to a count register 34, which accumulates the total number of pulses received and provides this information at an output lead 36. A second input lead 38 to the register 34 is provided to accept a signal which resets the accumulated count of the register 34 to zero.

The count register output 36, the output register input 38, and the chromatograph range and cycle outputs 12 and 14, respectively, are connected to a digital microprocessor 40. An additional output of microprocessor 40 is provided by a lead 42 as an additional input to the digital-to-analog converter 22. A further output is carried by a lead 44 to a digital-to-analog converter 46, whose output lead 48 is one input to a switch 50, the other input of which is the chromatograph electrometer output 17. The output lead 52 of the switch 50 is connected to a chart recorder 54. A lead 56 connects microprocessor 40 to readouts and controls shown at 58, and a further lead 59 connects the microprocessor to an alarm device 61.

The operation of this embodiment is as follows: When the forward phase of the operation of the chromatograph 10 begins, a signal so indicating is detected by the microprocessor 40. The microprocessor 40 provides periodically a signal over lead 38, setting count register 34 to zero, to prepare it to receive chromatograph output signal data.

The electrometer output 16 of the chromatograph 10 is added by the summing amplifier 18 to a feedback signal produced by the microprocessor 40 and provided to the amplifier 18 after conversion by the digital-to-analog converter 22. (This feedback signal will be discussed further below.) The resulting sum signal is smoothed by the filter 26 and fed to the voltage-to-frequency converter 30. This converter is a frequency modulated clock circuit, which produces pulses whose frequency is determined by the voltage of the signal from the chromatograph. For example, if the level of the signal received by the converter 30 varies from 0 to 10 volts, the frequency of the output of the converter 30 might vary from 0 to 1 megahertz. Measurement of the chromatograph output signal is based on the count value accumulated by the register over a fixed measuring period. In this embodiment, such period is preferably no longer than 100 milliseconds in length. At the end of each period, the microprocessor reads the state of the register 34 and resets the register to zero. The total count value accumulated by the register 34 during a given period represents the average value of the input signal to converter 30 during this period.

It should be noted that any high-frequency spikes or other electrical noise on the signal, if not removed already by the filter 26, would cause only very brief changes in the output frequency of the converter 30. Such changes being randomly positive and negative, they would tend to average out over the length of a measuring period, resulting in an insignificant noise-to-signal ratio.

Accuracy of measurement of the chromatograph signal is further enhanced by the brevity of the 100 millisecond measuring periods in comparison with the length of the peaks in the output signal, which are typically much longer. Thus any erroneous measurement occurring in a given period due to low-frequency noise, for example, would tend to be ignored as it would vary substantially from the relatively smooth curve formed on the chart recorder by prior and subsequent measurements.

During an initial period, for example 15 seconds, after the count register 34 is first reset, it is assumed that the output of the chromatograph tube consists entirely of carrier gas and that no hydrocarbon components of the test sample have yet been emitted. During this period, the signals transmitted to the microprocessor 40 over the lead 36 are treated as baseline data. The baseline signal is the output signal produced by a chromatograph in the absence of the introduction of a test sample, and therefore this baseline signal can be defined as any part of the output signal that is not a peak, a combined envelope of unseparated peaks, or a valley between nearby unseparated peaks.

Baseline data may vary from run to run because of a variety of factors, such as changes in the retarding effect of the column medium, temperature changes, condensation, or variations in the supply of carrier gas. During the first 15 seconds of each run, therefore, a new baseline level for that run is measured and memorized by the microprocessor 40.

Until the baseline level is measured, the feedback signal provided by the microprocessor 40 over the lead 42 is zero, and therefore the output on lead 24 of the summing amplifier 18 is equal to the output of the chromatograph 10. After measurement of the baseline level, however, the microprocessor 40 produces a feedback signal on lead 42 which is added to the chromatograph output so as to compensate for the baseline output of the chromatograph. For example, the feedback signal may be a digital signal that is converted by the digital-to-analog converter 22 into a signal whose magnitude is the negative of that of the baseline signal. In this situation, the input to the voltage-to-frequency converter 30 would be zero in the absence of a hydrocarbon component. Other arrangements would of course be possible.

As before stated, the chromatograph output level, that is, the count value of count register 34, is preferably sensed at least every 100 milliseconds. The microprocessor 40 then produces an output signal equal to the logarithm of the detected chromatograph signal. This signal is supplied by the lead 44 to the digital-to-analog converter 46, which produces an analog signal on lead 48 suitable for display on the chart recorder 54. A switch 50 is provided for switching between the logarithmic output of converter 46 and the unprocessed output of chromatograph 10 from output lead 17. Display of the unprocessed output would be useful, for example, in the event of a malfunction of the microprocessor or another processing component. The output of the switch 50 is connected by a lead 52 to the recorder 54.

It is desirable that the logarithmic scale of the graph produced by the chart recorder cover a dynamic range of four decades, thereby covering concentrations ranging from $10^2$ ppm to $10^6$ ppm. For concentrations between $10^1$ and $10^2$ ppm, the microprocessor automatically plots the converted chromatograph signal into a linear format on a linearly scaled portion of the chart. The proper range, linear or logarithmic depending on concentration, is selected on the basis of both the magnitude of the output signal as received via lead 36 and the electrometer sensitivity range of the chromatograph as sensed via lead 12. The alarm device 61 indicates if the permissible display range has been exceeded.

In addition to producing a graphic output for display, the microprocessor performs other functions as well. One of these is the detection of peaks in the chromatogram, that is, signals differing from the baseline signal, which indicate the passage of a component of the test sample under analysis through the detector. The peak detection method that is used by the digital apparatus of this embodiment is as follows: Each count value received from register 34 is stored and then replaced in storage with the succeeding count so long as comparison of the two counts indicates that they are ascending. When a descending count is detected, the baseline count is subtracted from the last ascending count. The difference is halved and added to the baseline count to determine a peak detection threshold. Should the descending trend continue and the count value fall below the computed peak detection threshold, then the largest ascending value will be considered to have been a peak value. Otherwise, the trend will be considered to have been a shoulder, and the process will be continued when the count value again ascends. Troughs in the waveform, and shoulders on the trailing edge of a peak are processed in a reverse manner.

Alternative signal processing routines are known to the art, for example those which detect peaks and troughs in a signal on the basis of an analysis of the smoothed slope of the waveform, and one of these may be used with this apparatus by changing the programming of the microprocessor.

When a peak has been detected, the desired data on the components of the sample, quantity and concentration data, for example, are determined by the microprocessor 40 and displayed on the readouts 58 via the lead 56. Another item that may be useful to be displayed is the elapsed time between the beginning of the forward phase and the detection of the peak.

A further item that may be displayed is the area between the output waveform and the baseline, i.e., the integral of the output waveform, between either baseline intersection points or troughs in the waveform. This integral, as before stated, represents the total detected quantity of the component. It should also be noted that if the total quantity of the sample is known, by a simple operation it can be arranged to determine and read out the percentage concentration of the detected component in the total sample. The integration can be carried out by any conventional method.

An additional feature included in the controls 58 of the embodiment is an input keypad for entry of calibration data corresponding to the known calibration gas mentioned previously. The calibration gas may have six peaks, for example, corresponding to carbon atomic numbers of one through six, occurring in sequence. Memory is provided to store the count values of register 34 corresponding to the peaks. The correct concentration of each component of the calibration gas is then entered, and the microprocessor determines therefrom appropriate factors to be applied to future measurements of the six peaks in order to determine the correct concentrations of the unknown test sample components.

The preceding embodiment achieves the desired objects of rejecting 60 Hertz line noise and minimizing the effect of detector noise by averaging it as the signal is averaged. Further, the disclosed digitization and logarithm computation apparatus is more accurate than analog systems. Finally, the use of a microprocessor allows virtually unlimited flexibility in changing the mode of signal analysis to meet future needs, and also reduces the cost of the device by having most functions performed by a preexisting microprocessor, thus requiring a minimum of new hardware.

Figure 2:
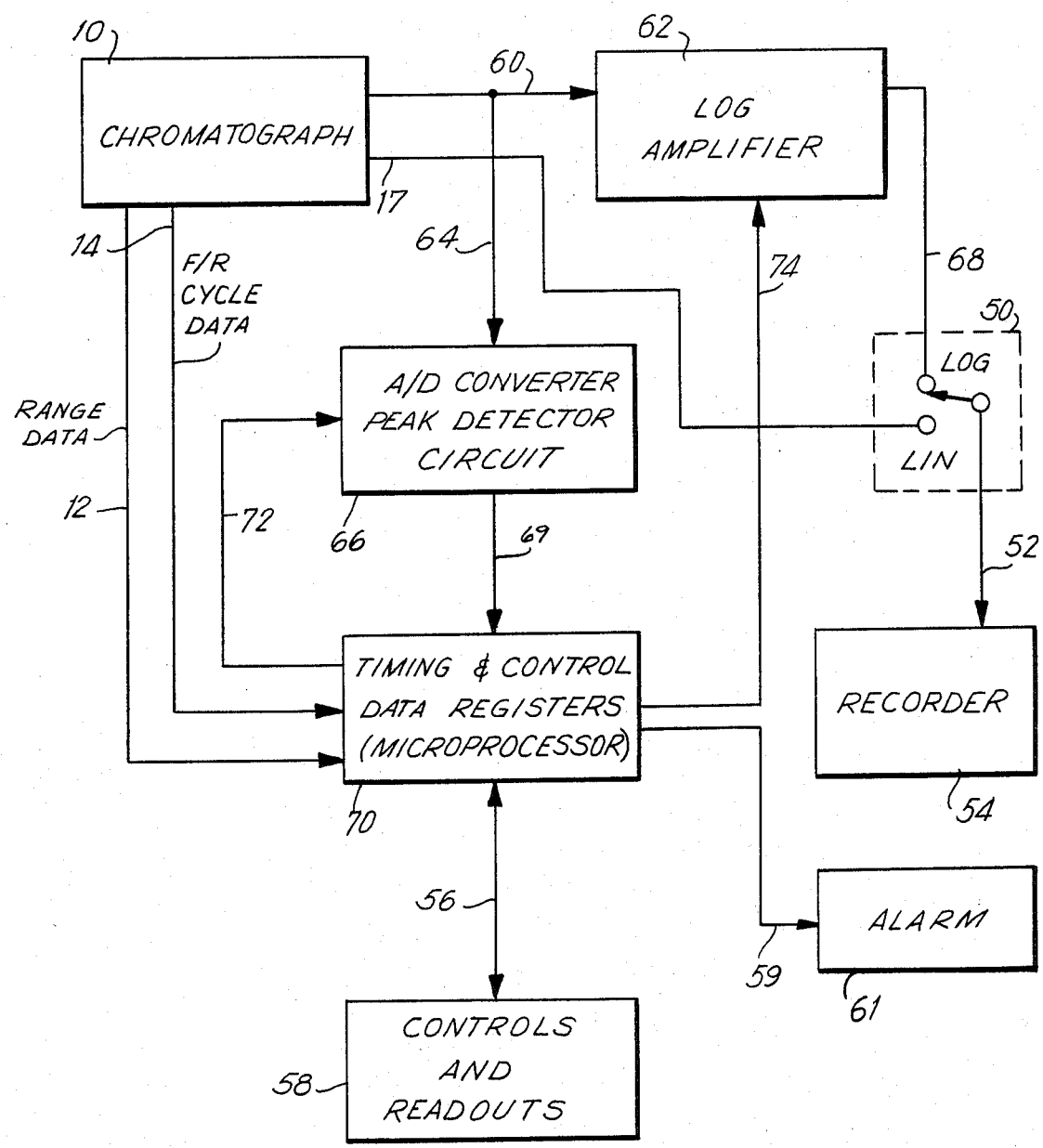

FIG. 2 shows another embodiment of the invention, which is particularly useful in applications where it is desired to have a logarithmic output, even if the microprocessor should fail. Only those features of this embodiment that differ from those of the previous embodiment will be described in detail.

In the embodiment of FIG. 2, the electrometer output signal of a chromatograph 10 is fed by a lead 60 to an analog logarithmic amplifier 62 and by a lead 64 to a peak detector and analog-to-digital converter 66. The output of the amplifier 62 is supplied by a lead 68 as one input of an output selecting switch 50, the other input of which is the output lead 17 of the chromatograph 10. The output of the detector-converter 66 is fed via a lead 69 to a digital microprocessor 70. Leads 72 and 74 connect additional outputs of the microprocessor 70 to, respectively, an additional input of the detector-converter 66, and an additional input of the amplifier 62.

In operation, the electrometer output signal of the chromatograph 10 is received via lead 64 by the detector-converter 66, which converts the signal to a digital signal usable by the digital microprocessor 70. It also detects peaks in the chromatograph output signal, by use of either digital circuitry, or a peak-sense-and-hold analog memory, or a conventional alternative thereto. The digitized signal and peak detection data are received over the lead 69 by the microprocessor 70, which performs resetting, processing, and output functions similar to those of the microprocessor 40 of the previous embodiment, being linked to a control input of the detector-converter 66 by the lead 72.

A further control output of the microprocessor 70 may be advantageously linked by the lead 74 to a control input of the logarithmic amplifier 62. This input receives scaling signals generated by the microprocessor on the basis of the magnitude of the digitized signal received on lead 69 and the electrometer sensitivity signal from lead 12. In the alternative, of course, manual switching may be provided if it is desired to set a desired scale of the output display. An alarm 61 connected to the microprocessor 70 by a lead 59 may also be provided.

Although the apparatus has been described and illustrated as having particular utility in connection with a gas chromatograph in the analysis and detection of hydrocarbons in drilling mud, it should be clear that the invention in its broadest aspects is not limited to this particular application, but rather is useful in the analysis or display of any electrical signal. Also, greater design and manufacturing efficiency may be achieved by integrating the interface electronics with the processor electronics, while retaining the same general functional relationships.

Considering the breadth of usefulness of the invention for signal processing, the terms and expressions that have been employed herein are used as terms of description and not of limitation, and there is no intention in the use of such terms and expressions of excluding any equivalents of the features shown and described or portions thereof, but it is recognized that various modifications are possible within the scope of the invention as claimed.

What is claimed is:

1. Apparatus for processing an input signal from a chromatograph, comprising:
   logarithmic means connected to the chromatograph for receiving said input signal and producing a logarithmic signal which is indicative of the logarithm of said input signal;
   detecting means connected to the chromatograph for receiving said input signal, detecting peaks therein, and producing a signal indicating the occurrence of said peaks; and means connected to said logarithmic and detecting means for providing said logarithmic signal and said indicating signal as outputs of said processing apparatus.

2. Apparatus for processing an input signal from a chromatograph, comprising:

logarithmic means connected to the chromatograph for receiving said input signal and producing a logarithmic signal which is indicative of the logarithm of said input signal;

detecting means connected to the chromatograph for receiving said input signal, detecting peaks therein, and producing a signal indicating the occurrence and amplitude of said peaks; and means connected to said logarithmic and detecting means for providing said logarithmic signal and said indicating signal as outputs of said processing apparatus.

3. Apparatus for processing an input signal from a chromatograph, comprising:

a first converter connected to the chromatograph for receiving said input signal and producing clock signals whose frequency is representative of the input signal;

a count register connected to said first converter for counting the clock signals and accumulating a count value;

means connected to said count register for resetting said count value to an initial value at the commencement of successive measuring periods of preselected length; and a second converter connected to said count register and to said resetting means for producing a signal representative of said count value, and for providing said count value signal at the termination of said measuring periods as an output of the processing apparatus, said second converter comprising a programmed digital microprocessor, and a digital-to-analog converter connected thereto for receiving a digital output of the microprocessor representing said count value signal and providing an analog siganl as said output of the processing apparatus.

4. Apparatus as defined in claim 3, wherein said second converter produces a feedback signal; and further comprising:

a summing amplifier connected to the chromatograph and to the second converter for receiving the input signal from the chromatograph and the feedback signal and producing an output representative of their sum; and a filter connected to the summing amplifier for receiving the sum signal and providing a filtered output signal;

the input signal received by the first converter being the filtered outut signal.

5. Apparatus for processing an input signal from a chromatograph, comprising:

a first converter connected to the chromatograph for receiving said input signal and producing clock signals whose frequency is representative of the input signal;

a count register connected to said first converter for counting the clock signals and accumulating a count value;

means connected to said count register for resetting said count value to a predetermined initial value at the commencement of successive measuring periods of predetermined length; and a second converter connected to said count register and said resetting means for producing a logarithmic signal representative of the logarithm of said count value and for providing said logarithmic signal at the termination of said measuring periods as an output of the processing apparatus.

6. Apparatus as defined in claim 5, wherein said second converter comprises a programmed digital microprocessor, and a digital-to-analog converter connected thereto for receiving the digital output of the microprocessor and providing an analog logarithmic signal as an output of the processing apparatus.

7. Apparatus for processing an input signal from a chromatograph, comprising:

a first converter connected to the chromatograph for receiving said input signal and producing clock signals whose frequency is representative of the input signal;

a count register connected to said first converter for counting the clock signals and accumulating a count value;

means connected to said count register for resetting said count value to a predetermined initial value at the commencement of successive measuring periods of predetermined length;

a second converter connected to said count register and said resetting means for producing a logarithmic signal representative of the logarithm of said count value and for providing and logarithmic signal at the termination of said measuring periods as an output of the processing apparatus, said second converter producing a feedback signal;

a summing amplifier connected to the chromatograph and to the second converter for receiving the input signal from the chromatograph and the feedback signal and producing an output representative of their sum; and a filter connected to the summing amplifier for receiving the sum signal and providing a filtered output signal;

the input signal received by the first converter being the filtered output signal.

8. Apparatus as defined in claim 7, wherein said second converter comprises a programmed digital microprocessor and digital-to-analog converters connected to the latter for receiving the digital output of the microprocessor and providing analog logarithmic and feedback signals.

9. Apparatus as defined in claim 8, further comprising means connected to the chromatograph for supplying the input signal as an additional output of the processing apparatus.

10. Apparatus as defined in claim 3, further comprising means connected to the chromatograph for sensing the sensitivity of the chromatograph and for providing a signal indicative of said sensitivity as an additional output of the processing apparatus.

11. Apparatus as defined in claim 8, wherein said measuring periods are no greater than 100 milliseconds in length.

12. Apparatus as defined in claim 7, wherein the operation of the chromatograph comprises at least a forward phase, and further comprising means connected to the chromatograph for sensing the occurrence of said phase.

13. Apparatus as defined in claim 12, wherein the second converter further comprises:
   means for initiating said resetting of the count value to an initial value when a forward phase of the chromatograph operation has begun;
   means for averaging the count value during a succeeding period of predetermined length after said resetting to determine a baseline count and for storing said baseline count, said feedback signal being representative of said baseline count;
   means for detecting the occurrence of an increase followed by a decrease in the difference between the count value and said stored baseline count and for identifying said occurrence as a peak in the count value; and
   means for providing as an additional output of the processing apparatus a signal to indicate the elapsed time between the first resetting of the count value and the occurrence of the peak.

14. Apparatus as defined in claim 13, wherein the second converter further comprises means for detecting troughs in the count value, and means for storing successive accumulated count values, integrating the stored values accumulated in the intervals between successive troughs, and providing the result of the integration as an additional output of the processing apparatus.

15. Apparatus as defined in claim 14, wherein the processor is further programmed for:
   detecting the occurrence of an increase followed by a decrease in the difference between the count value and said stored baseline count, identifying said occurrence as a peak in the count value, and providing as an additional output of the processing apparatus a signal to indicate the elapsed time between the first resetting of the count value and the occurrence of the peak; and
   detecting troughs in the count value, storing successive accumulated count values, integrating the stored values accumulated in the intervals between successive troughs, and providing the result of the integration as an additional output of the processing apparatus.

16. Apparatus for processing an input signal from a chromatograph, comprising:
   a first converter connected to the chromatograph for receiving said input signal and producing clock signals whose frequency is representative of the input signal;
   a count register connected to said first converter for counting the clock signals and accumulating a count value;
   means connected to said count register for resetting said count value to a predetermined initial value at the commencement of successive measuring periods of predetermined length;
   a second converter connected to said count register and said resetting means for producing a logarithmic signal representative of the logarithm of said count value and for providing said logarithmic signal at the termination of said measuring periods as an output of the processing apparatus, the second converter comprising:
   means for detecting peaks and troughs in the count value, and means for measuring the elapsed time between said resetting and the occurrences of succeeding peaks, and producing time signals representative of said elapsed times; and
   means for storing successive accumulated count values, integrating the stored values accumulated between the occurrences of successive troughs, and producing an integral signal representative of the result of such integration; and
   said apparatus further comprises means connected to the second converter for providing as additional outputs of the processing apparatus said time and integral signals.

17. Apparatus for processing an input signal from a chromatograph, wherein the operation of the chromatograph includes at least a forward phase, comprising:
   means connected to the chromatograph for providing the input signal as an output of the processing apparatus;
   a summing amplifier connected to the chromatograph for adding a plurality of signals and producing a signal representative of their sum, said input signal from the chromatograph being one of the plurality of signals;
   a filter connected to the summing amplifier for receiving the sum signal and providing a filtered output signal;
   a frequency converter connected to the filter for receiving said filtered output signal and producing clock signals whose frequency is representative of the filtered output signal;
   a count register connected to the frequency converter for counting the clock signals and accumulating a count value;
   a digital processor connected to the chromatograph, to the count register, and to the summing amplifier, and two digital-to-analog converters connected to the processor, said processor being programmed for:
   detecting when a forward phase of the chromatograph operation has begun and performing a first resetting of the count value to a predetermined initial value in response to said detection;
   averaging the count value during an averaging period of predetermined length after said first resetting to determine a baseline count and storing said baseline count;
   resetting the count value to a predetermined initial value at the beginning of successive measuring periods of a predetermined length following said averaging period;
   detacting the sensitivity of the chromatograph;
   producing a feedback signal representative of the baseline count, the feedback signal being provided through one of said digital-to-analog converters as an additional input to the summing amplifier; and
   producing a logarithmic signal representative of the count value and providing at least the logarithmic signal at the end of the measuring periods through the other of said digital-to-analog converters as an additional output of the processing apparatus.

18. Apparatus for processing an input signal from a chromatograph, comprising:
   means connected to the chromatograph for initiating said processing;
   logarithmic means connected to the chromatograh for receiving the input signal and producing a logarithmic output signal which is equal to the logarithm of the input signal;

means connected to the chromatograph for detecting peaks and troughs in the input signal;

timing means connected to the detecting means and to the initiating means for determining the elaped times between said initiation of processing and the occurrence of said peaks, and for providing signals indicative of said times;

integrating means connected to the chromatograph and to the detecting means for integrating the value of the input signal over the intervals between successive troughs, and for providing signals indicative of the result of the integration; and means connected to the logarithmic, timing, and integrating means for providing the logarithmic output signals, the elapsed time signals, and the integral signals as outputs of the processing apparatus.

19. Apparatus as defined in claim 18, further comprising means connected to the chromatograph for supplying the input signal as an additional output of the processing apparatus.

20. Apparatus as defined in claim 18, further comprising means connected to the chromatograph for sensing the sensitivity of the chromatograph and for providing an additional output of said processing apparatus indicative of said sensitivity.

21. Apparatus as defined in claim 18, wherein said initiating, timing, and integrating means comprises a digital processor.

22. Apparatus as defined in claim 18, wherein the operation of the chromatograph comprises at least a forward phase; and wherein the initiating means comprises means connected to the chromatograph and to the timing means for sensing the beginning of said forward phase and for initiating the operation of the timing means when the beginning of said forward phase is sensed.

23. Apparatus for processing an input signal from a chromatograph whose operation comprises at least a forward phase, comprising:

means connected to the chromatograph for sensing the beginning of said forward phase and for producing an initiating signal in response thereto;

a logarithmic amplifier connected to the chromatograph for receiving the input signal and producing a logarithmic output signal which is representative of the logarithm of the input signal;

means connected to the chromagraph for detecting peaks and troughs in the input signal;

a digital processor connected to the chromatograph, to the detecting means, and to the initiating means, programmed for sensing the sensitivity of the chromatograph and producing signals indicative thereof; and the processing apparatus further comprising means connected to the chromatograph, to the logarithmic amplifier, and to the digital processor for providing at least the logarithmic output signal as an output of the processing apparatus.

24. Apparatus as defined in claim 23, the digital processor being further programmed for:

determining the elapsed times between said initiating signal and the occurrence of said peaks, and for providing signals indicative of said times; and integrating the value of the input signal over the intervals between successive troughs and providing signals indicative of the result of the integration;

the processing apparatus further comprising means connected to the chromatograph, to the logarithmic amplifier, and to the digital processor for providing the elasped time signals and the integral signals as outputs of the processing apparatus.

* * * * *